United States Patent [19]

DeMarinis et al.

[11] Patent Number: 4,496,558

[45] Date of Patent: Jan. 29, 1985

[54] PHARMACEUTICAL COMPOSITIONS AND METHODS FOR PRODUCING ALPHA ANTAGONISM

[75] Inventors: Robert M. DeMarinis, Ardmore; Jacob P. Hieble, Philadelphia; William D. Matthews, West Chester, all of Pa.

[73] Assignee: Smithkline Beckman Corporation, Philadelphia, Pa.

[21] Appl. No.: 461,058

[22] Filed: Jan. 26, 1983

Related U.S. Application Data

[63] Continuation-in-part of Ser. No. 325,249, Nov. 27, 1981, abandoned, and Ser. No. 398,015, Jul. 14, 1982.

[51] Int. Cl.$^3$ .............................................. A61K 31/33
[52] U.S. Cl. .................................................... 514/213
[58] Field of Search ........................................ 424/244

[56] References Cited

U.S. PATENT DOCUMENTS

| | | | |
|---|---|---|---|
| 2,520,264 | 8/1950 | Walter | 424/244 |
| 3,716,639 | 2/1973 | Hoegerle et al. | |
| 3,752,892 | 8/1973 | Hoegerle et al. | |
| 3,795,683 | 3/1974 | Brossi et al. | 424/244 |
| 3,906,006 | 9/1975 | Brossi et al. | 260/465 D |
| 4,065,473 | 12/1977 | Brossi et al. | 424/244 |
| 4,210,749 | 7/1980 | Shetty | |
| 4,233,217 | 11/1980 | Shetty | |
| 4,265,890 | 5/1981 | Holden et al. | |

FOREIGN PATENT DOCUMENTS 1268243  3/1972  United Kingdom .

OTHER PUBLICATIONS

Chem. Abst. 76, 14311 (h), (1972), Pecherer et al.
Principles of Med. Chemistry–W. O. Foye, editor, (1976)—p. 350—Lea & Febiger—Philadelphia, Pa.

*Primary Examiner*—Douglas W. Robinson
*Attorney, Agent, or Firm*—Joseph A. Marlino; Stuart R. Suter; Alan D. Lourie

[57] ABSTRACT

Pharmaceutical compositions and methods for producing alpha$_2$ antagonism utilize, as active ingredients, 6-halo-N-substituted 2,3,4,5-tetrahydro-1H-3-benzazepines. These compositions are particularly useful for lowering intraocular pressure and for the treatment of abnormal cardiovascular conditions such as, for example, congestive heart failure, angina pectoris and thrombosis. The compositions and compounds of this invention, also, produce a reduction in blood pressure in hypertensive subjects and are, therefore, useful as antihypertensive agents.

13 Claims, No Drawings

PHARMACEUTICAL COMPOSITIONS AND METHODS FOR PRODUCING ALPHA ANTAGONISM

This is a continuation-in-part of U.S. Ser. No. 325,249 now abandoned and Ser. No. 398,015 filed Nov. 27, 1981 and July 14, 1982, respectively.

This invention relates to pharmaceutical compositions and methods for producing alpha$_2$ antagonism by employing certain 6-halo-N-substituted 2,3,4,5-tetrahydro-1H-3-benzazepines.

The pharmaceutical compositions and methods of this invention produce alpha$_2$ antagonism, a pharmacological action which is associated with the reduction of intraocular pressure and a broad spectrum of beneficial cardiovascular activity. For example, the compounds of this invention are used for treating congestive heart failure, angina pectoris and thrombosis.

Further, the compounds produce a reduction in abnormally high blood pressure and are, therefore, useful as antihypertensive agents. This invention also relates to a method of producing antihypertensive activity by administering these compounds internally.

Reduction of intraocular pressure is of significant importance in the treatment of glaucoma which is a disease of the eye characterized by increased intraocular pressure. Glaucoma is a leading cause of blindness in people over forty. In poorly controlled glaucoma, the intraocular pressure is persistently increased and there is a progressive retinal and optic nerve degeneration. If untreated, a red painful eye may occur accompanied by reduced vision and, eventually, blindness.

The three agents most commonly used in glaucoma therapy are pilocarpine, timolol or epinephrine. Pilocarpine causes miosis and spasm of the ciliary muscle which produces blurred vision and myopia. Epinephrine dilates the pupil and blurs the vision as well as induces hyperemia, macular edema and allergic reactions in the eye. Moreover, systemic absorption of epinephrine after ocular instillation has produced cardiac arrhythmias. Timolol has few notable ocular side effects but systemic actions of the drug are a problem. Bradycardia, syncope, exacerbation of borderline congestive heart failure and bronchospasm have all been reported after topical timolol administration.

A still further disadvantage associated with epinephrine is that it is unstable to both air and light and subject to chemical attack by many agents that are conventionally used in pharmaceutical preparations. Attempts made to overcome these disadvantages usually resulted in compositions that were irritating to the body tissues or formed biologically inactive derivatives thereof.

It is, therefore, one object of this invention to produce ophthalmic compositions and methods for lowering intraocular pressure which lack direct effect on pupil size, have no effect on heart rate or blood pressure in normotensive animals and minimal local or systemic adverse effects upon instillation into the eye.

The novel compositions and methods for using them described hereafter have been found unexpectedly to reduce intraocular pressure without the undesirable side effects and disadvantages of the prior art agents noted above.

BACKGROUND OF THE INVENTION

U.S. Pat. Nos. 4,210,749 and 4,233,217 disclose a broad class of benzazepines being useful as analgesics, antihistaminics and narcotic antagonists. However, there is no specific disclosure of the compounds of Formula I. Moreover, there is no suggestion in these patents that the compounds of Formula I would be useful as alpha$_2$ antagonists. One specific compound of Formula I, 6-chloro-3-methyl-2,3,4,5-tetrahydro-1H-3-benzazepine has been disclosed as a chemical intermediate in U.S. Pat. No. 4,265,890. There is no suggestion in this patent that the compound has any useful biological activity. U.S. Pat. Nos. 3,716,639 and 3,752,892 disclose 7-chloro and 6-chloro-2,3,4,5-tetrahydro-1H-3-benzazepines as anorexigenic agents.

None of the above known art discloses the biological activities of the claimed compositions and methods.

DESCRIPTION OF INVENTION

The 6-halo-N-substituted 2,3,4,5-tetrahydro-1H-3-benzazepine compounds which are the active ingredients of the pharmaceutical compositions of this invention are represented by the following formula:

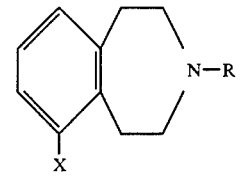

Formula I in which:

R is lower alkyl of from 1 to 3 carbon atoms or allyl; and

X is halogen, or a pharmaceutically acceptable acid addition salt thereof.

A particularly preferred compound in the pharmaceutical compositions and methods of this invention is a compound of Formula I in which R is methyl and X is chloro being the compound, 6-chloro-3-methyl-2,3,4,5-tetrahydro-1H-3-benzazepine or an acid addition salt thereof.

The above compounds of Formula I which are the active ingredients in the compositions and methods for producing alpha$_2$ antagonism are prepared by synthetic methods familiar to the art. One procedure is as follows:

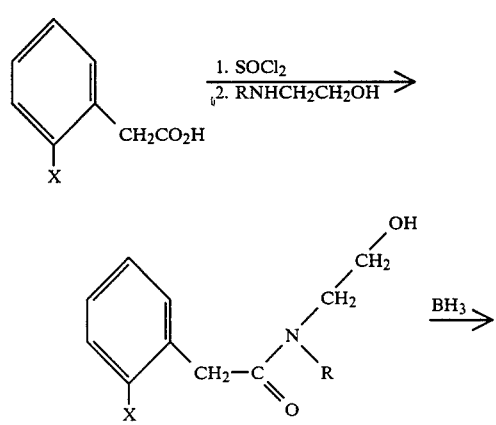

-continued

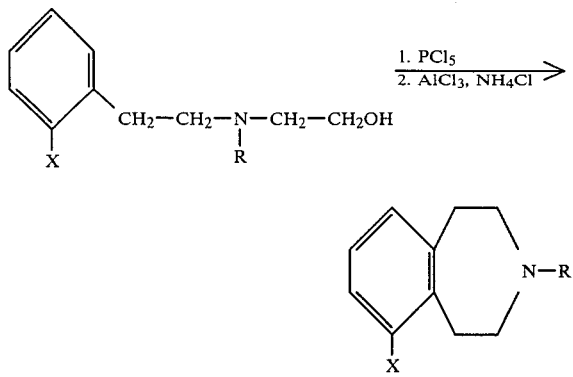

The terms X and R are as defined above.

According to the above procedure, a halophenyl acetic acid is treated with thionyl chloride followed by an appropriate amino alcohol. The resultant amide is reduced by any well known keto reducing agent such as, for example, borane. The resultant amino alcohol is then converted to the corresponding halide, such as chloride or bromide, and cyclized under Friedel-Crafts conditions. The cyclization step is carried out using Lewis acids, such as, for example, aluminum chloride, aluminum bromide, titanium chloride and antimony chloride. Advantageously, the cyclization is carried out in a melt of aluminum chloride and ammonium chloride at elevated temperatures.

The compounds of Formula I are also prepared by reacting a 3-benzazepine compound in which R is hydrogen with an alkylating or acylating reagent which will replace the hydrogen with the desired R group. Such reagents include compounds of the formula RY and RCOY wherein R is as defined above for Formula I and Y is halogen, such as chloro or bromo.

Other alkylating agents include aldehydes or ketones under reductive reaction conditions. The reduction can be accomplished catalytically, such as with hydrogen and platinum, or chemically, such as with sodium borohydride or sodium cyanoborohydride.

When the reagent of the formula RCOY is employed, the carbonyl moiety is subsequently reduced with, for example, lithium aluminum hydride.

The pharmaceutically acceptable, nontoxic, acid addition salts having the utility of the free bases of Formula I, prepared by methods well known to the art, are formed with both inorganic or organic acids, for example: maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

The activity of the compounds of Formula I is demonstrated in vitro by determining the prejunctional alpha₂ antagonist activity using the isolated superfused guinea pig left atrium. Briefly, the heart is removed from a pentobarbital-anesthetized male guinea pig. The left atrium is removed, dissected free of extraneous tissue and mounted in a 2 ml. superfusion chamber. The tissue is paced at 60 pulse/minute and the sympathetic nerves excited at 6 minute intervals by field stimulation. The response to nerve stimulation is measured as the difference in contractile force between the basal contraction and peak contraction following a nerve stimulation. A concentration-response curve for clonidine (alpha₂ agonist) is prepared by administering an increasing concentration of clonidine following each successive stimulation. The tissue is then superfused with the alpha₂ antagonist to be tested for thirty minutes and the clonidine concentration-effect curve was repeated in the presence of antagonist. The receptor dissociation constant of the antagonist ($K_B$) is defined as the antagonist concentration required to shift the log concentration-response curve of the agonist to the right by a factor of 2.

Selectivity for the alpha₂ vis-a-vis the alpha₁-adrenoceptor is determined by comparing the $K_B$ obtained as described above with the $K_B$ on the alpha₁ receptor determined in the rabbit ear artery segment as an antagonist of the constrictor response induced by norepinephrine. (Hieble and Pendleton, Arch. Pharmacol., 309, 217–224 (1979)).

A preferred compound of this invention is 6-chloro-3-methyl-2,3,4,5-tetrahydro-1H-3-benzazepine as the hydrochloride salt which has a $K_B$ value in the isolated perfused guinea pig left atrium of 13 nM.

When substitution is present at the 7-position of the benz-ring, a dramatic reduction in activity results. For example, the 7-chloro-3-methyl-2,3,4,5-tetrahydro-1H-3-benzazepine has a $K_B$ value of 150 nM, i.e., about one tenth the alpha₂ antagonist activity of the 6-chloro derivative. Further, when a substituent such as amino is present at the 6-position of the benz-ring, or the 6 and 7 positions are fused to a cyclopentane ring, the compounds are completely inactive as alpha₂ antagonists.

The antihypertensive activity of the compounds of this invention is demonstrated in vivo as follows:

Male rats (300–450 g.) are anesthetized with sodium brevital and the femoral vein and artery are cannulated. Cannulas are run intradermally so as to be externalized in the dorso-sacral area of either side and kept in place by wound clips. The rats are allowed to regain consciousness after being placed in a small animal restrainer. The arterial cannula is connected to a pressure transducer for constant blood pressure and heart rate monitoring. Drugs are administered either orally via gavage or i.v. via the femoral vein cannula at a rate of 0.06 ml./minute.

The above test is conducted on both normotensive and hypertensive rats. DOCA Salt hypertensive rats are prepared from male uninephrectomized Sprague-Dawley rats. The rats, approximately six weeks of age, are lightly anesthetized with ether and subcutaneously implanted with a 25-mg. deoxycorticosterone acetate pellet in the left dorso-sacral area. Six days later a second pellet is implanted in the right dorso-sacral area. These rats are fed a normal laboratory diet, but are given 1% saline solution to drink in place of water. The rats are kept on the saline drinking water for 22–24 days.

The following table sets forth the effect of 6-chloro-3-methyl-2,3,4,5-tetrahydro-1H-3-benzazepine as the hydrochloride salt on blood pressure after i.v. administration to both normotensive and hypertensive rats.

TABLE 1

| | Diastolic Blood Pressure | | |
| | | Decrease BP (MMHg) | |
| Type of Rats | PreDrug | 0.5 mg./Kg. | 0.1 mg./Kg. I.V. |
| --- | --- | --- | --- |
| Normotensive (control) | 95 ± 7 MMHg | 6 ± 2 | 13 ± 1 |

TABLE 1-continued

| Type of Rats | Diastolic Blood Pressure | | |
|---|---|---|---|
| | | Decrease BP (MMHg) | |
| | PreDrug | 0.5 mg./Kg. | 0.1 mg./Kg. I.V. |
| (Sprague-Dawley) (n = 4) DOCA Salt Hypertensive (n = 4) | 135 ± 5 MMHg | 27 ± 3 | 33 ± 4 |
| Normotensive (control) (Wistar-Kyoto) (n = 4) | 115 ± 3 MMHg | 7 ± 2 | 10 ± 2 |
| Spontaneously Hypertensive (n = 7) | 167 ± 3 MMHg | 33 ± 7 | 46 ± 2 | n = Number of rats

The data in Table 1 demonstrate that while 6-chloro-3-methyl-2,3,4,5-tetrahydro-1H-3-benzazepine has little effect on diastolic blood pressure in normotensive rats, it produced a marked drop in diastolic blood pressure in both DOCA Salt and spontaneously hypertensive rats. Moreover, comparison of the 0.5 mg./kg. and 1.0 mg./kg. doses shows that the antihypertensive effect is dose-related.

The effect of the oral administration of 6-chloro-3-methyl-2,3,4,5-tetrahydro-1H-3-benzazepine hydrochloride on blood pressure in the DOCA-salt hypertensive rat was also determined. Table 2 below sets forth the results of this test.

TABLE 2

| Dose (PO) | Mean Arterial Pressure | | Δ BP (MM Hg) |
|---|---|---|---|
| | Pre-Drug | Post-Drug | |
| 2 mg/kg | 148 ± 11 | 131 ± 12 | 17 ± 3 |
| 5 mg/kg | 160 ± 7 | 127 ± 5 | 34 ± 4 |
| 10 mg/kg | 167 ± 8 | 99 ± 4 | 68 ± 8 |

Therefore, the compositions and methods of this invention are antihypertensive rather than hypotensive which means, in the context of this disclosure, that they are effective in abnormal states only. Further, the 6-chloro-3-methyl congener of Formula I has been demonstrated not to induce postural hypotension as does prazosin. No limiting side effects have been detected in a dose range procedure.

In addition, for cardiovascular use, the 3-benzazepine active ingredient in the compositions of this invention may be combined with a clinically effective dose of a known cardiovascular agent such as a thiazide diuretic, for example hydrochlorothiazide, or triamterene, or a calcium channel blocker, for example verapamil, bepridil, diltiazem or nifedipine, or a β-adrenergic blocker, for example propranolol, timolol or atenolol, or an angiotensin-converting enzyme inhibitor, for example captopril.

The amount of the substituted 3-benzazepine active ingredient in such compositions of this invention would be selected from the range noted below for cardiovascular activity combined with, for example, from about 2 mg. to about 250 mg. of the thiazide component. When combined with triamterene, from about 5 mg. to about 250 mg. of triamterene would be present. When a calcium channel blocker is employed in the compositions of this invention, from about 1 mg. to about 500 mg. would be employed. In a combination with an angiotensin-converting enzyme inhibitor from about 10 mg. to about 150 mg. of the inhibitor would be present.

A further activity of the compounds of this invention is demonstrated by their ability to reduce intraocular pressure as noted above. The measurement of intraocular pressure depends on subjecting the eye to a force that indents or flattens it. Either the effect of a particular force or the force for a given effect is measured. The specific procedure employed for the compounds of this invention is a normal rabbit intraocular pressure determination. A solution of 0.5% proparacaine hydrochloride diluted 1:10 with physiological saline is instilled into the eye of a rabbit. The lids are gently massaged over the cornea to insure good distribution of the solution. The eye is exposed by separating the lids and the tip of a probe is slowly placed on the cornea at the point where the curvature of the cornea is the greatest, i.e., on the optic axis. Employing an Alcon Applanation Pneumatonograph, the intraocular pressure is determined in each eye until a stable reading is obtained. West, C., Capella, J. and Kaufman, H., Am. J. Opthalmol. 74:505 (1972).

Nine rabbits are used in each study, three animals for each dose in most circumstances. An initial, t=0, intraocular determination is made in both eyes. Immediately following the initial reading, the formulations to be tested, comprising concentrations of 0.01 to 10% of active ingredient, are instilled and pressure readings are taken at 0.5, 1, 2, 3, 4, and 6 hours post-instillation. The intraocular pressure is determined from the value recorded on the pneumotonograph chart paper. A mean intraocular pressure value is calculated at each time point. A preferred compound of this invention, 6-chloro-3-methyl-2,3,4,5-tetrahydro-1H-3-benzazepine as the hydrochloride salt, decreased intraocular pressure at one hour by 3.5 mm. of mercury relative to the untreated eye.

When the chloro was moved to the 7-position of the benzazepine nucleus and the resulting 7-chloro position isomer was administered at the same doses, there was no lowering of intraocular pressure.

In summary, the structures of the compounds of this invention are specifically identified by having the halo at the 6-position of the benzazepine nucleus. As noted from the results of the test for alpha$_2$ antagonism and the lowering of intraocular pressure, this is a critical feature of the compounds of this invention in order to obtain the desired biological activity.

It was also unexpectedly discovered that when the preferred compound, 6-chloro-3-methyl-2,3,4,5-tetrahydro-1H-3-benzazepine as the hydrochloride salt, was given systemically and the above procedure was followed, intraocular pressure was lowered with no significant effect on systemic blood pressure. When 0.5 mg./kg. of the 6-chloro-3-methyl compound was infused in the ear vein of conscious normotensive rabbits, the compound decreased intraocular pressure at one hour by between 4 and 5 mm. of mercury. Further, the 6-chloro-3-methyl-benzazepine compound when given orally to rabbits at doses of up to 5 mg./kg. significantly decreased the intraocular pressure. At an oral dose of 5 mg./kg. the 6-chloro-3-methyl-benzazepine compound decreased intraocular pressure at one hour by between 4 and 5 mm of mercury.

The pharmaceutical compositions for oral or parenteral administration used to carry out the method of producing systemic alpha$_2$ antagonism and the resulting antihypertensive activity comprise a pharmaceutical carrier and, as the active ingredient, a benzazepine compound of Formula I. The active ingredient will be present in the dosage unit compositions in a nontoxic effective amount to produce systemically effective alpha$_2$ antagonism and the resultant cardiovascular activity.

Preferably, the compositions contain the active ingredient of Formula I in a quantity selected from the range of from about 25 mg. to about 500 mg., advantageously from about 50 mg. to about 250 mg., per dosage unit.

The pharmaceutical carrier may be, for example, a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200-400) and water. The carrier or diluent may include a time delay material well known to the art such as, for example, glyceryl monostearate or glyceryl distearate alone or with a wax.

A wide variety of pharmaceutical dosage units can be employed, for example, the preparation may take the form tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of producing alpha$_2$ antagonism according to this invention comprises administering to a subject in need thereof a nontoxic amount sufficient to produce alpha$_2$ antagonism of a 3-benzazepine compound of Formula I.

Preferably, the compounds of Formula I are administered in conventional dosage unit forms for oral, parenteral or anal administration and prepared by combining an appropriate dose of the compound with a pharmaceutical carrier.

The active ingredient of Formula I will normally be administered in a daily dosage regimen selected from about 100 mg. to about 1000 mg., most preferably from about 200 mg. to about 500 mg. Advantageously, equal doses will be administered, preferably, one to four times per day.

Advantageously, the pharmaceutical compositions of this invention which reduce intraocular pressure comprise a pharmaceutical carrier, preferably an ophthalmic vehicle, and, as the active ingredient, a 6-halo-N-substituted 2,3,4,5-tetra-hydro-1H-3-benzazepine of Formula I. The active ingredient will be present in the compositions of this invention in an effective amount to reduce intraocular pressure.

Preferably, the compositions of this invention for ocular administration will contain from about 0.01% to about 5.0% of the active ingredient of Formula I measured as the base, advantageously, from about 0.03% to about 3.0%.

The ophthalmic vehicle or carrier will be, for example, a liquid or solid. Exemplary of liquid ophthalmic carriers include standard 1.9% isotonic boric acid, 0.9% sodium chloride, or sodium borate solutions. Further, conventional phosphate buffer solutions such as the Sorenson phosphate buffer having a pH of 6.8 may be employed as the carrier. Exemplary of solid ophthalmic carriers are typical ointment bases such as petrolatum.

The compositions of the present invention are conventionally administered topically to the eye in dosage unit forms, such as, for example, ophthalmic solutions, ointments, creams, gels, or dispersions. When controlled release of the compound is desired, it may alternatively be incorporated into polymeric ocular insert systems which are well known to the art such as, for example, U.S. Pat. No. 4,052,505.

The ophthalmic solutions are sterile and can contain, in addition to the compound of Formula I, antimicrobial agents as preservatives. Exemplary of such agents are the quaternary ammonium germicides such as benzalkonium chloride, benzethonium chloride or cetylpyridium chloride. Other such agents that can be employed are chlorobutanol or phenylmercuric nitrate. If antioxidants are required, sodium sulfite, sodium ascorbate or other ophthalmologically acceptable antioxidants known to the art, such as oxime sulfate, may be used.

The preferred method of reducing intraocular pressure according to this invention comprises topically administering to an animal an amount sufficient to reduce intraocular pressure of an N-substituted 2,3,4,5-tetrahydro-1H-3-benzazepine compound of Formula I.

The benzazepine compound is administered to the eye for prophylactic or curative treatment of glaucoma in ophthalmological dosage unit forms prepared by combining an appropriate dose of the compound with the above noted ophthalmological carriers. Preferably the ophthalmic dosage form is applied from two to four times daily. When an ophthalmic solution is employed one to five drops may be administered to each eye two to four times a day.

When administered internally for the lowering of intraocular pressure, the 3-benzazepine compound of Formula I may be employed in any of the pharmaceutical dosage units listed above for producing alpha$_2$ antagonism.

When the administration is carried out as described above, alpha$_2$ antagonism is manifested in at least two ways, systemically for antihypertensive or other beneficial cardiovascular activity and locally or systemically for lowering intraocular pressure.

The following examples are not limiting but are illustrative of the compounds of this invention and processes for their preparation. The temperatures are in degrees Centigrade.

EXAMPLE 1

A mixture of 125 g. (0.73 mol) of O-chlorophenylacetic acid, 155 g. (1.3 mol) of thionyl chloride and 2-3 drops of dimethylformamide in 1500 ml. of toluene was stirred at room temperature for three hours. The toluene was evaporated under reduced pressure to give an oil which was dissolved in 200 ml. of methylene chloride. This was added dropwise to a solution of 165 g. (2.2 mol) of N-methylamino ethanol in 1 liter of methylene chloride. After addition was complete, the solution was stirred at room temperature for three hours. The organic solution was washed with water, dilute hydrochloric acid and saturated sodium chloride, dried over magnesium sulfate, filtered and evaporated to give 2-chloro-N-(2-hydroxyethyl)-N-methylbenzene acetamide as a crystalline solid, m.p. 77°.

To 400 ml. of a 1 mol solution of borane in tetrahydrofuran was added dropwise a solution of 43 g. of the above amide in 350 ml. of tetrahydrofuran at a rate sufficient to maintain a gentle reflux. After addition was complete, the solution was refluxed for two hours, cooled in an ice bath and treated carefully with dilute hydrochloric acid to destroy excess borane. The majority of the solvent was removed under vacuum and the residue heated on a steam bath for one hour. The mixture was diluted with 300 ml. of water and extracted with ether. The aqueous layer was made basic with 40% sodium hydroxide and extracted with ether. The combined basic extracts were washed with water and saturated sodium chloride, dried and evaporated to give 2-[[2-(2-chlorophenyl)-ethyl]-methylamino]ethanol.

A suspension of 36 g. (0.173 mol) of phosphorous pentachloride in 300 ml. of methylene chloride was treated dropwise with a solution of 37 g. (0.173 mol) of the 2-[[2-(2-chlorophenyl)ethyl]methylamino]ethanol in 150 ml. of methylene chloride. After addition was complete, the mixture was refluxed overnight, evaporated to dryness and partitioned between dilute hydrochloric acid and ether. The aqueous layer was made basic with 10% sodium hydroxide and extracted well with ether. The ether extracts were washed with water and saturated sodium chloride, dried over magnesium sulfate and filtered. Addition of a saturated solution of ethereal hydrogen chloride gave a solid precipitate which was removed by filtration, washed with ether and dried to give 2-chloro-N-(2-chloroethyl)-N-methylbenzene ethanamine hydrochloride, m.p. 110°.

To a mixture of 41.5 g. (0.155 mol) of the above chloro ethanamine hydrochloride and 6.26 g. (0.117 mol) of ammonium chloride was added 41 g. of anhydrous aluminum chloride. The reaction became homogeneous, melted and exothermed. It was placed in an oil bath which had been heated to 175° and stirred for thirty minutes. An additional 20 g. of aluminum chloride was added and the mixture heated for another thirty minutes. A final 41 g. portion of aluminum chloride was added and the reaction heated for twenty hours. It was cooled to 140° and poured into 3 l. of ice water containing 300 ml. of concentrated hydrochloric acid and stirred for fifteen minutes. Sixty grams of sodium potassium tartrate was added and stirred until solution was effected. It was made basic with 40% sodium hydroxide, extracted twice with ether and the combined extracts washed with water, and saturated sodium chloride, dried and reduced in volume by half. Addition of a solution of saturated ethereal hydrogen chloride gave a solid precipitate which was collected, washed with ether and dried to give a white solid. Crystallization from methanol-ethyl acetate gave 6-chloro-3-methyl-2,3,4,5-tetrahydro-1H-3-benzazepine hydrochloride, m.p. 268°–270°.

EXAMPLE 2

A stirred solution of 1.2 g. of 6-chloro-3-methyl-2,3,4,5-tetrahydro-1H-3-benzazepine in 30 ml. of toluene was treated at 50° by dropwise addition with a solution of 0.7 g. cyanogen bromide in 25 ml. of toluene. Following the addition, the mixture was stirred and heated at 50° for one hour. A stream of nitrogen was passed over the surface of the solution during the reaction. The mixture was cooled, filtered and the filtrate concentrated in vacuo to yield 6-chloro-3-cyano-2,3,4,5-tetrahydro-1H-3-benzazepine melting at 81°–82° from hexane-ether solution.

The 6-chloro-3-cyano-2,3,4,5-tetrahydro-1H-3-benzazepine was refluxed for 19 hours in a mixture of 30 ml. of glacial acetic acid and 30 ml. of 6N hydrochloric acid. The mixture was concentrated in vacuo to yield 6-chloro-2,3,4,5-tetrahydro-1H-3-benzazepine as the hydrochloride salt of m.p. 214°–215° from ethanol. This salt in turn gave the base 6-chloro-2,3,4,5-tetrahydro-1H-3-benzazepine on treatment with dilute sodium hydroxide solution.

EXAMPLE 3

A mixture of 0.52 g. of 6-chloro-2,3,4,5-tetrahydro-1H-3-benzazepine, 0.34 g. of allyl bromide, 0.6 g. of potassium carbonate and 20 ml. of 90% ethanol was stirred at room temperature for 17 hours. The mixture was filtered and the filtrate concentrated in vacuo. The residue was extracted with 35 ml. of ether and the ethereal extract treated with isopropanolic hydrogen chloride to precipitate 3-allyl-6-chloro-2,3,4,5-tetra-hydro-1H-3-benzazepine hydrochloride. Recrystallization of this salt from absolute ethanol gave 3-allyl-6-chloro-2,3,4,5-tetrahydro-1H-3-benzazepine hydrochloride having a melting point of 248°–249°.

EXAMPLE 4

A solution of 1.5 g. of 6-chloro-2,3,4,5-tetrahydro-1H-3-benzazepine, 2.0 g. of acetic anhydride and 20 ml. of pyridine was stirred at room temperature for 3 hours. The mixture was concentrated in vacuo and the residue washed with 3N hydrochloric acid, then water, to yield 3-acetyl-6-chloro-2,3,4,5-tetrahydro-1H-3-benzazepine melting at 64°–66°. This amide was reduced in ether with a 50% excess of lithium aluminum hydride at reflux for 6 hours. Upon decomposition of excess reducing agent, the reaction mixture was filtered and the ethereal filtrate dried over magnesium sulfate. The filtrate was treated with ethereal hydrogen chloride solution to precipitate 6-chloro-3-ethyl-2,3,4,5-tetrahydro-1H-3-benzazepine as the hydrochloride salt which melted at 274°–275° from absolute alcohol.

EXAMPLE 5

Following the procedure of Example 1 and substituting 2-[[2-(2-chlorophenyl)ethyl]ethylamino]ethanol and 2-[[2-(2-chlorophenyl)ethyl]allylamino]ethanol for 2-[[2-(2-chlorophenyl)ethyl]methylamino]ethanol yields the following respective products: 6-chloro-3-ethyl-2,3,4,5-tetrahydro-1H-3-benzazepine and 6-chloro-3-allyl-2,3,4,5-tetrahydro-1H-3-benzazepine.

EXAMPLE 6

Substituting O-bromophenylacetic acid and O-fluorophenylacertic acid as starting materials for O-chlorophenylacetic acid and following the procedure of Example 1 yields 6-bromo-3-methyl-2,3,4,5-tetrahydro-1H-3-benzazepine hydrochloride and 6-fluoro-3-methyl-2,3,4,5-tetrahydro-1H-3-benzazepine hydrochloride respectively.

EXAMPLE 7

| Ingredients | % W/W |
|---|---|
| 6-Chloro-3-Methyl-2,3,4,5-Tetrahydro-1H—3-Benzazepine Hydrochloride | 2.5 g. |
| Benzalkonium Chloride | 0.02 g. |
| Sodium Bisulfite | 0.10 g. |
| Sterile Sodium Chloride Solution (0.9%) USP qs | 100 ml. |

The ingredients are dissolved in the sodium chloride solution. The solution is sterilized by filtration and aseptically packaged.

Two drops are instilled in the eye three times a day to treat glaucoma.

EXAMPLE 8

| Ingredients | % W/W |
| --- | --- |
| 6-Chloro-3-Methyl-2,3,4,5-Tetra-hydro-1H—3-Benzazepine | 1.0 g. |
| Purified White Petrolatum, U.S.P. qs | 100.0 g. |

Under aseptic conditions, the benzazepine is thoroughly incorporated in the petrolatum and packaged.

The ointment is applied topically to the eye to treat glaucoma four times a day.

EXAMPLE 9

| Ingredients | Amounts |
| --- | --- |
| 6-Chloro-3-Methyl-2,3,4,5-Tetrahydro-1H—3-Benzazepine Hydrochloride | 150 mg. |
| Lactose | 350 mg. |

The ingredients are mixed and filled into a hard gelatin capsule.

One capsule is administered orally four times a day to a hypertensive subject.

EXAMPLE 10

| Ingredients | Amounts |
| --- | --- |
| 6-Chloro-3-Methyl-2,3,4,5-Tetrahydro-1H—3-Benzazepine Hydrochloride | 200 mg. |
| Calcium Sulfate Dihydrate | 150 mg. |
| Sucrose | 25 mg. |
| Starch | 15 mg. |
| Talc | 5 mg. |
| Stearic Acid | 3 mg. |

The calcium sulfate dihydrate, sucrose and the benzazepine are thoroughly mixed and granulated with 10% gelatin solution. The wet granules are screened, dried and then mixed with the starch, talc and stearic acid, screened and compressed into a tablet.

One tablet is administered orally three times a day to a hypertensive subject.

EXAMPLE 11

| Ingredients | Amounts |
| --- | --- |
| 6-Chloro-3-Methyl-2,3,4,5-Tetrahydro-1H—3-benzazepine hydrochloride | 100 mg. |
| Hydrochlorothiazide | 50 mg. |
| Lactose | 155 mg. |

The ingredients are mixed and filled into gelatin capsules.

One capsule is administered orally three times a day.

EXAMPLE 12

| Ingredients | Amounts |
| --- | --- |
| 6-Chloro-3-methyl-2,3,4,5-tetrahydro-1H—3-benzazepine hydrochloride | 150 mg. |
| Captopril | 50 mg. |
| Lactose | 100 mg. |

The ingredients are mixed and filled into a hard gelatin capsule.

One capsule is administered orally twice a day.

We claim:

1. A pharmaceutical composition for product alpha$_2$ antagonism comprising a pharmaceutically acceptable carrier and a nontoxic, effective amount to produce said antagonism of a 3-benzazepine compound of the formula:

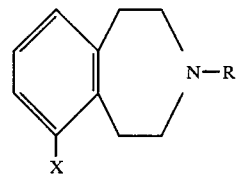

in which:

R is allyl; and

X is halogen;

or a pharmaceutically acceptable, acid addition salt thereof.

2. A pharmaceutical composition for producing antihypertensive activity comprising a pharmaceutically acceptable carrier and a nontoxic, antihypertensive effective amount of a 3-benzazepine compound of claim 1.

3. The pharmaceutical composition of claim 2 in which X is chloro.

4. The composition of claim 3 in which the compound is in the form of its hydrochloride salt.

5. The pharmaceutical composition of claim 1 in which X is chloro.

6. The composition of claim 5 in which the 3-benzazepine is in the form of its hydrochloride salt.

7. A method of producing alpha$_2$ antagonist activity in a subject in need of such activity comprising administering to said subject a nontoxic amount sufficient to produce said activity of a 3-benzazepine compound of the formula:

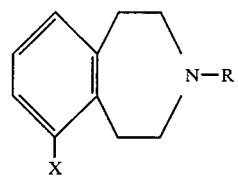

in which:

R is allyl; and

X is halogen;

or a pharmaceutically acceptable, acid addition salt thereof.

8. The method of claim 7 in which X is chloro.

9. The method of claim 8 in which the compound is in the form of its hydrochloride salt.

10. A method of producing antihypertensive activity in a hypertensive subject comprising administering to said subject a nontoxic amount sufficient to produce said activity of a 3-benzazepine compound of claim 7.

11. The method of claim 10 in which said compound is administered orally or parenterally in a nontoxic, antihypertensive amount selected from the range of about 50 mg. to 250 mg. administered from about 2 to 4 times daily.

12. The method of claim 10 in which X is chloro.

13. The method of claim 12 in which the compound is in the form of its hydrochloride salt.

* * * * *